United States Patent [19]

Buchwald et al.

[11] Patent Number: 5,220,020

[45] Date of Patent: Jun. 15, 1993

[54] CATALYTIC REDUCTION OF ORGANIC CARBONYLS USING METAL CATALYSTS

[75] Inventors: Stephen L. Buchwald, Somerville, Mass.; Alberto Gutierrez, Rockville, Md.; Scott C. Berk, Somerville; Kristina A. Kreutzer, Cambridge, both of Mass.

[73] Assignee: Massachusetts Institute of Technology, Cambridge, Mass.

[21] Appl. No.: 792,233

[22] Filed: Nov. 14, 1991

Related U.S. Application Data

[63] Continuation-in-part of Ser. No. 749,111, Aug. 23, 1991, abandoned, which is a continuation-in-part of Ser. No. 616,892, Nov. 21, 1990.

[51] Int. Cl.$^5$ ............... C07C 29/136; C07C 29/50; C07D 207/30; C07D 265/30; C07D 333/16
[52] U.S. Cl. ..................... 544/106; 544/146; 548/560; 549/78; 564/463; 564/305; 564/375; 564/416; 564/495; 568/700; 568/799; 568/846; 568/861; 568/862; 568/864; 568/877; 568/878; 568/881; 568/884; 568/892; 568/909.5; 568/914; 568/814
[58] Field of Search ............... 568/700, 799, 846, 861, 568/862, 864, 877, 878, 881, 884, 892, 909.5, 914, 814; 564/463, 749, 111, 616, 892, 305, 375, 416, 495; 544/106, 146; 548/560; 549/78

[56] References Cited

U.S. PATENT DOCUMENTS 3,061,424  10/1962  Nitzsche et al. ............... 564/416 X
3,984,374  10/1976  Cooper et al. ............... 564/463

OTHER PUBLICATIONS

Cp$_2$Ticl$_2$-Catalyzed Grignard Reactions. 3. Reactions with Esters: Efficient Methoddology for the Synthesis of Secondary Alcohols and for the Reduction of Esters to Primary Alcohols., Sato et al., (Tetrahedron Letters, 1980 21, 2175).
Improved Procedure for the Selective Reduction of Carbonyl Compounds and Carboxylic Acid Esters by Potassium Salt-Induced Hydrosilylation, Chuit et al. (Synthesis, 1981 558).
Some New Methods in Organic Synthesis, Corriu, et al. (Tetrahedron, 1983 39, 999).
Bis(n$^5$-cyclopentadienyl)diphenyltitanium-catalyzed Hydrosilylation of Ketones Nakano et al., (Chem. Lett., 1988, 481).
Sur Quelques Aspects De La Reactivite Des Hydrogenosilanes En Chimie Organique, Calas (Pure Appl. Chem. 1966, 13, 61).
Reduction with Trichlorosilane, Nagata, et al. (J. Org. Chem., 1973, 38, 795).
A New Method for the Reduction of Esters, Boyer et al. (Synthesis, 1981, 558).
"Synthetic Strategy for the Coupling of the Calicheamicin Oligosaccharide with Aglycons: Synthesis of Dynemicin A-Calicheamicin Hybrid Structures" Nicolaou et al. (Agnew. Chem. Int. Ed. Engl. 30 (1991) No. 5, pp. 585-588).
Beletskaya, et al., Bulletin of the Academy of Sciences of the USSR, Division of Chemical Science, vol. 3, No. 3, Part 2 (Sep., 1990), pp. 613-614.
Chuit et al., *Synthesis*, 1982, pp. 981-984.
Boyer et al., *Synthesis*, 1981, pp. 558-559.
Sato et al., Tetrahedron Letters, vol. 21, pp. 2175-2178, vol. 21, pp. 2175-2178.
Nakano et al., *Chemistry Letters*, 1988, pp. 481-484.
Lipowitz, et al. Aldrichima Acta, vol. 6, p. 1 (1973).

*Primary Examiner*—Floyd D. Higel
*Attorney, Agent, or Firm*—Thomas J. Engellenner; William C. Geary, III

[57] ABSTRACT

A process is provided whereby organic carbonyl substrates, including esters, lactones, ketones, amides and imides are reduced in a reaction with a silane reducing reagent and a catalyst. Exemplary catalysts include metal alkoxides and metal aryloxides.

16 Claims, No Drawings

CATALYTIC REDUCTION OF ORGANIC CARBONYLS USING METAL CATALYSTS

BACKGROUND OF THE INVENTION

The U.S. Government has rights in this invention pursuant to National Science Foundation Grant Number CHE-9000842 and NIH Grant GM 34917.

RELATED APPLICATION

This application is a continuation-in-part of U.S. patent application Ser. No. 749,111, filed Aug. 23, 1991, entitled "Catalytic Reduction of Organic Carbonyls Using Metal Catalysts," now abandoned which is a continuation-in-part of U.S. patent application Ser. No. 616,892, filed Nov. 21, 1990, entitled "Catalytic Reduction of Organic Carbonyls."

The present invention relates to processes for catalytically reducing and/or transforming organic carbonyl compounds.

Methods currently are known for the reduction of organic carbonyls. Many such reduction reactions, such as those involving esters, ketones and amides, utilize lithium aluminum hydride or related species as a reducing reagent. Such reagents are quite pyrophoric and can ignite spontaneously upon contact with air or water. Moreover, lithium aluminum hydride typically is dispensed in a volatile liquid such as ether, thus compounding safety concerns. Aside from potential safety issues which surround the use of reducing reagents such as lithium aluminum hydride, their use can be costly as these compounds must be used in stoichiometric rather than catalytic quantities. A further disadvantage of reactions which use lithium aluminum hydride as a reducing agent is that they yield an aluminum salt as a by-product, from which the desired end product is often difficult to isolate.

Reactions which reduce organic carbonyls, such as esters, ketones and amides, often are commercially quite significant, as they can be used in the large scale preparation of pharmaceuticals and specialty chemicals. Thus, the safety and economy of the reduction reactions are important considerations. Accordingly, it would be advantageous to provide safer and more economical processes for reducing organic carbonyl compounds.

It is thus an object of the invention to provide a safer and more economical process for reducing organic carbonyl compounds such as esters, lactones, ketones and amides. Another object is to provide such a reaction where the end product of the reaction is effectively and conveniently isolated. It is also an object to provide a catalytic reduction process for organic carbonyls which utilizes self-activating, air-stable catalysts. Other objects will be apparent upon reading the disclosure which follows.

SUMMARY OF THE INVENTION

The invention provides a relatively safe and effective catalytic process for conveniently reducing organic carbonyl compounds, including esters, lactones, ketones, amides and imides. The applicability of this process to the manufacture of pharmaceuticals and specialty chemicals will be appreciated by those having ordinary skill in the art. Among the organic carbonyls which can be reduced by the processes of this invention are esters, lactones, ketones, amides and imides. The method of the invention reduces esters and ketones to alcohols, lactones to diols, and amides to amines. In another embodiment of the invention, tertiary amides having an alpha hydrogen can be reduced to yield enamines, which may be converted to aldehydes. In addition, imides can be reduced to dienamines.

The term "catalyst" is used interchangeably herein to refer both to the metal complexes or precatalysts before their activation as catalytic species, and to the active catalytic species themselves.

Generally, the process of the invention involves providing in a suitable reaction vessel an excess of a silane reducing agent together with the desired substrate, and a catalytic amount (i.e., about 3 to 10 percent by mole relative the amount of substrate) of a catalyst. This mixture is heated to the desired temperature and the reduction reaction is allowed to proceed to completion. The order in which substrate, catalyst and reducing reagent are added to the reaction vessel generally is not critical.

Catalysts suitable for use in practicing this invention are described herein. Preferably these catalysts are self-activating in the presence of a silane, and can be air-stable.

In reductions of esters, lactones, and ketones by this reaction, a silicon-containing intermediate is produced. The silicon is cleaved from the intermediate by conventional techniques, after quenching of the catalyst, to yield a crude end product in a more reduced form than the starting compound. The end product may then be purified by known techniques. Reduction reactions in which the carbonyl substrate is an amide or imide do not require a silicon cleavage step. Following the reduction of an amide or imide one need only perform conventional separation and purification techniques to yield the desired end product.

DETAILED DESCRIPTION OF THE INVENTION

The disclosures of U.S. patent application Ser. Nos. 749,111, filed Aug. 23, 1991, and 616,892, filed Nov. 21, 1990, are incorporated by reference herein.

The process of the invention can be used to catalytically reduce organic carbonyl compounds such as esters, lactones, ketones, amides and imides. Esters and ketones can be reduced to alcohols, and lactones can be reduced to diols. Tertiary amides having no alpha hydrogens can be reduced to amines. Tertiary amides having alpha hydrogens can be reduced to enamines, which can be converted to aldehydes by known techniques. Additionally, imides can be reduced to dienamines.

One important feature of the process of the invention is that it utilizes relatively inexpensive and safe catalysts and reducing reagents. In addition, the catalysts used in the method of the invention are self-activating in the presence of a silane, and need not be maintained in an organic solvent, although the reaction may be carried out in the presence of an organic solvent if desirable Further, because the catalysts generally are air stable, the reduction reaction can often be carried out in an ambient atmosphere, rather than in an inert atmosphere.

The basic steps of the invention generally involve placing the substrate, catalyst and reducing agent in a suitable reaction vessel and heating to between 25° C. and 80° C. in order to react the substrate and reducing agent. The reaction normally requires from about 1 to 24 hours to complete. The catalyst can be quenched to terminate the reaction. Standard work-up and separation procedures are then effected to yield the end product of the reaction, having a high level of purity typically greater than about 95%.

In one embodiment, the silane reducing agent, the substrate and the catalyst are all added, sequentially, to a reaction vessel which has been placed in an oil bath preheated to the desired temperature at which the reaction will be conducted.

The order in which the reactants and catalyst are added to the reaction vessel is not critical. However, the silane reducing agent and substrate may be added first. Following heating, the catalyst can then be added. In other embodiments it is possible to add the substrate first. Variations of the order in which reactants and catalysts can be added to the reaction vessel are illustrated herein.

The reduction reaction of the present invention can be carried out in an ambient atmosphere or in an atmosphere of an inert gas such as nitrogen or argon. While in many instances the reaction works equally well in either type of atmosphere, it may be preferable (except for reductions of tertiary amide substrates), at least from a safety standpoint, to carry out the reduction reaction in an ambient atmosphere to avoid the production of silane gas.

In one general procedure, the reaction vessel can first be charged with silane reducing agent, substrate and catalyst. The reaction mixture is heated to a temperature at which the reaction is to occur (i.e., 25° C. to 80° C.) while it is stirred. The reaction is allowed to proceed until all of the substrate is consumed, as may be verified by GLC analysis of a sample of the reaction mixture. When the substrate is consumed, the reaction mixture is cooled to room temperature. Thereafter, work-up and separation procedures are effected as the reaction mixture is added to a solvent such as tetrahydrofuran (THF). Aqueous sodium hydroxide can then be added to this mixture followed by stirring for 1 to 2 hours. The reaction mixture can then be added to a water/ether mixture, shaken, and separated. The aqueous layer is washed with ether, and the ether extracts are dried over MgSO$_4$ and concentrated to give the product. This reaction can be conducted in an inert gas such as argon, or in an ambient atmosphere.

According to one alternate procedure for performing the present reduction reaction, a reaction vessel, such as a Schlenk tube, is heated to a suitable temperature (25° C. to 80° C.) and is charged with silane reducing agent, substrate, and catalyst, and the reaction mixture is stirred while the desired temperature is maintained. The reaction may also be conducted in a flask equipped with a drying tube which includes an agent such as anhydrous CaSO$_4$. This method is generally well suited to reactions which will be conducted in an ambient atmosphere.

As noted above, the invention is generally applicable to the reduction of organic carbonyl substrates. Exemplary carbonyl substrates include esters, lactones, ketones, amides and imides. The invention is also potentially applicable to the reduction of compounds such as aldehydes, acids, acid chlorides, acid anhydrides, nitriles and thioesters.

During the reduction of esters lactones and ketones a silicon-containing intermediate compound is obtained. The silicon may be cleaved from the intermediate by a variety of known extraction techniques to isolate the desired end product of the reduction reaction. For example, silicon cleavage may be effected by treatment with alcoholic or aqueous solutions of hydrochloric acid or sodium hydroxide which has been admixed with a small amount of tetrahydrofuran. Subsequently, separation and drying techniques can be utilized to recover the crude product, which, if necessary, can then be purified by conventional techniques such as chromatography or distillation. The reductions of tertiary amides and imides do not require a silicon cleavage step. However, separation and purification techniques generally must be effected to recover the desired end product.

A variety of catalysts can be used effectively in the reduction reactions of the present invention. Exemplary catalysts broadly include those having the general formulas:

$$M(L)(L')(L'') \quad (1)$$
$$M(L)(L')(L'')(L''') \quad (2)$$
$$M(L)(L')(L'')(L''')(L^{iv}) \quad (3)$$
$$M(L)(L')(L'')(L''')(L^{iv})(L^{v}) \quad (4)$$

where M is a group 3, 4, 5 or 6 metal, a lanthanide, or an actinide and where L, L', L'', and L''', L$^{iv}$ and L$^{v}$, independently, can be some combination of H, an alkyl group, an aryl group, a silyl group, a halogen, —OR, —SR, or —NR(R'), where R and R' may be H or an alkyl or aryl group and may be different or the same. Examples of group 3, 4, 5 or 6 metals which may be useful with the present invention include titanium, vanadium, niobium, chromium, yttrium, scandium, lanthanum. Examples of useful lanthanides include samarium, ytterbium, and lutetium. Examples of useful actinides include thorium and uranium. Titanium, however, is the most preferred metal.

Among the catalysts generally identified above, the most preferred include metal alkoxides and metal aryloxides, such as titanium alkoxides and titanium aryloxides. Exemplary catalysts include titanium (IV) isopropoxide, titanium (IV) ethoxide, trichlorotitanium (IV) isopropoxide, titanium (IV) methoxide, titanium (IV) butoxide, niobium (V) ethoxide, neodymium (III) isopropoxide, dysprosium (III) isopropoxide, and yttrium (III) isopropoxide.

Currently, the most preferred catalysts include titanium (IV) isopropoxide, titanium (IV) ethoxide and trichlorotitanium (IV) isopropoxide.

Among the particular advantages of the catalysts identified above are their properties of self-activation in the presence of a silane and their air stability. The temperature at which the catalysts should be maintained ranges from about 25° C. to 80° C.

The catalysts are present in the reaction in catalytic quantities, ranging from about 5–10 mole percent, relative to the substrate.

As noted above, the reducing reagent preferred in the present processes is a silane compound with at least one hydrogen bonded to the silicon. Exemplary silane compounds which may be used in these processes are represented by the formulas shown below.

$$R(R')SiH_2 \quad (5)$$
$$RSiH_3 \quad (6)$$
$$RO(R'O)SiH_2 \quad (7)$$

$$(RO)-\underset{\underset{(OR')}{|}}{\overset{\overset{(OR'')}{|}}{Si}}-H \quad (8)$$

where R, R' and R" represent hydrogen, alkyl or aryl groups and may be the same or different. Specific examples of suitable silane reducing reagents include diphenylsilane, phenylsilane, diethylsilane, dimethylsilane, triethoxysilane, trimethoxysilane, and poly(methylhydrosiloxane).

Preferably, the silane reducing reagent is used in an amount ranging from about 100 to about 300 percent by mole as compared to the amount of the substrate.

As noted above, the reduction reaction can be used to reduce ester and ketone substrates to alcohols. Also, lactone substrates can be reduced to yield diols, and amides can be reduced to amines. In addition, imides can be reduced to dienamines.

In an alternative embodiment, tertiary amides having an alpha hydrogen may be reduced to cyclic or acyclic enamine compounds. The enamines which result may be converted to aldehydes by standard techniques such as hydrolysis with dilute aqueous acid.

The invention is further illustrated by the examples which follow.

Experimental Procedure for the Titanium Alkoxide Catalyzed Reduction of Esters to Alcohols General Procedure I: A dry flask equipped with a drying tube (anhydrous $CaSO_4$) and a magnetic stir bar was immersed in a 40° C. oil bath and charged with triethoxysilane (1.38 mL, 7.5 mmol) and the ester (3 mmol). Then, titanium (IV) isopropoxide (45 µL, 0.15 mmol) was added, and the reaction mixture was stirred at 40° C. until GLC analysis of an aliquot taken from it showed complete disappearance of the ester (usually, about 4 to 18 hours). The reaction mixture was cooled to room temperature and added to THF (7 mL). Aqueous NaOH (1 N, 15 mL) was then added to the solution. After vigorous stirring at room temperature for 1–4 hours, the reaction mixture was added to a water/ether mixture (50 mL each), shaken vigorously, and separated. The aqueous layer was washed with an additional 50 mL of ether, and the combined ether extracts were dried over $MgSO_4$. Concentration in vacuo afforded pure (often greater than 95% as estimated by NMR) product.

EXAMPLE 1 (REDUCTION OF ETHYL DECANOATE)

General procedure I was followed to reduce ethyl decanoate (696 µL, 3 mmol). The reduction took 6.5 hours at 40° C. Work-up yielded 441 mg (93% yield) of decanol as a clear oil.

EXAMPLE 1-A (REDUCTION OF ETHYL DECANOATE)

A dry Schlenk tube under argon was charged with titanium (IV) ethoxide (32 µL, 0.15 mmol) and triethoxysilane (1.39 mL, 7.5 mmol) and heated to 40° C. After 15 min., ethyl decanoate (696 µL, 3 mmol) was added. After 18 hours, the reaction was determined to be complete by GC analysis. Standard work-up afforded 444 mg (93% yield) of decanol as a clear oil.

EXAMPLE 2 (REDUCTION OF ETHYL 6-BROMOHEXANOATE)

General procedure I was followed to reduce ethyl 6-bromohexanoate (553 µL, 3.1 mmol). The reduction took 4 hours at 40° C. Work-up yielded 525 mg (97% yield) of 6-bromohexanol as a clear oil.

EXAMPLE 3 (REDUCTION OF METHYL 10-UNDECENOATE)

General procedure I was followed to reduce methyl 10-undecenoate (594 mg, 3 mmol). The reduction took 9 hours at 40° C. Work-up yielded 431 mg (85% yield) of 10-undecen-1-ol as a clear oil.

EXAMPLE 4 (REDUCTION OF ETHYL 2-THIOPHENEACETATE)

General procedure I was followed to reduce ethyl 2-thiopheneacetate (7.2 mL, 48 mmol), except that 22.0 mL (120 mmol) of triethoxysilane was added and 720 µL (2.4 mmol) titanium (IV) isopropoxide was added, and the temperature of the oil bath was 52° C. The reduction took 4 hours at 52° C. Work-up yielded 5.8 g (95% yield) of 2-(thienyl)-ethanol as a pale yellow oil.

EXAMPLE 5 (REDUCTION OF ETHYL 2-PHENYLETHANOATE)

General procedure I was followed to reduce ethyl 2-phenylethanoate (478 µL, 3 mmol). The reduction took 4 hours at 40° C. Work-up yielded 348 mg (95% yield) of phenethyl alcohol as a clear oil.

EXAMPLE 6 (REDUCTION OF ACETOPHENONE TO SEC-PHENETHYL ALCOHOL)

A dry Schlenk tube under argon was charged with triethoxysilane (1.1 ml, 6.0 mmol) and acetophenone (580 µL, 5 mmol) and heated to 48° C. Titanium (IV), isopropoxide (75 µL, 0.25 mmol) was then added. After stirring at 48° C. for an hour the color changed to deep blue. After 6 hours the reaction mixture was cooled to room temperature. After 12 hours it was added to THF (5 mL). Aqueous NaOH (1 N, 15 mL) was then added to the solution. After vigorous stirring at room temperature for 1 hour, the reaction mixture was added to a water/ether mixture (100 mL each), shaken vigorously, and the organic layer was separated. The aqueous layer was washed with an additional 100 mL of ether, and the combined ether extracts were dried over $MgSO_4$. Concentration in vacuo afforded 587 mg (97% yield, greater than 95% pure by NMR and GC) of sec-phenethyl alcohol as a slightly yellowish oil.

EXAMPLE 7 (REDUCTION OF 2-OCTANONE TO 2-OCTANOL)

A dry Schlenk tube under argon was charged with triethoxysilane (1.4 ml, 7.5 mmol) and 2-octanone (525 µL, 5 mmol) and heated to 60° C. Titanium (IV) isopropoxide (75 µL, 0.25 mmol) was then added. After stirring at that temperature for an hour the color changed to deep blue. After 12 hours the reaction mixture was cooled to room temperature and added to THF (5 mL). Aqueous NaOH (1 N, 15 mL) was then added to the solution. After vigorous stirring at room temperature for 1 hour, the reaction mixture was added to a water/ether mixture (100 mL each), shaken vigorously, and separated. The aqueous layer was washed with an additional 100 mL of ether, and the combined ether extracts were dried over $MgSO_4$. Concentration in vacuo afforded 401 mg (63% yield, greater than 95% pure by NMR and GC) of 2-octanol as an oil.

EXAMPLE 8 (PREPARATION OF 4-(2-PHENYLETHENYL) MORPHOLINE)

4-(2-phenylacetyl) morpholine (0.410 g, 2.0 mmol) was dissolved in $C_6H_6$ (5 mL) under a nitrogen atmosphere and then triethoxysilane (0.92 mL, 5.0 mmol) and titanium (IV) isopropoxide (0.03 mL, 0.1 mmol) were added. The reaction mixture was heated to 60° C. for 15 hours. The $C_6H_6$ was removed in vacuo and the resulting cream colored solid was dissolved in warm (60° C.) hexane (3 mL). The hexane solution was cooled to room temperature, and cream colored crystals appeared in the flask. The recrystallization flask was put in an acetone-filled dewar, which was cooled to −78° C. overnight. The hexane solution was decanted from the cream colored crystals which were dried in vacuo, and 0.38 g of product was collected, although $^1H$ NMR showed the presence of a silicon byproduct. The material was dissolved in 3 mL of warm hexane (60 ° C.) and slowly cooled to room temperature. The hexane was decanted and the product was dried in vacuo to produce 0.24 g (63% yield) of 4-(2-phenylethenyl) morpholine as a cream colored solid.

EXAMPLE 9 (PREPARATION OF 4-(2-[2-THIENYL]ETHENYL) MORPHOLINE)

4-(2-[2-thienyl]acetyl) morpholine (0.42 g, 2.0 mmol) was dissolved in $C_6H_6$ (4 mL) and then triethoxysilane (0.92 mL, 5.0 mmol) and titanium (IV) isopropoxide (0.03 mL, 0.1 mmol) were added. The reaction mixture was heated to 60 ° C. for 15 hours. The $C_6H_6$ was removed in vacuo and the resulting yellow solid was dissolved in warm (60° C.) hexane (4 mL). The hexane solution was cooled to room temperature, and yellow crystals appeared in the flask. The recrystallization flask was put in an acetone-filled dewar, which was cooled to −78° C. overnight. The hexane solution was decanted from the yellow crystals. The crystals were washed with cold hexane (3 mL) and recrystallized from hot (60° C.) hexane. The flask containing the crystals was put in an acetone-filled dewar, which was cooled to −78° C. The hexane was decanted and the crystals were washed with 2 portions of cold hexane (1 mL). The crystals were dried in vacuo and 0.28 g (74% yield) of 4-(2-[2-thienyl]ethenyl) morpholine, as yellow crystals, was collected.

EXAMPLE 10 (PREPARATION OF N,N-DIMETHYL BENZYLAMINE)

N,N-dimethylbenzamide (0.49 g, 3.0 mmol), triethoxysilane (1.4 mL, 7.5 mmol), titanium (IV) isopropoxide (0.04 mL, 0.15 mmol), and $C_6H_6$ (0.5 mL) were added to a flask open to the air and capped with a $CaSO_4$ drying tube. The reaction mixture was heated to 60° C. for 16 hours. The solvent was removed in Vacuo and the contents were added to a mixture of 1 M NaOH (20mL) and THF (10mL). This mixture was stirred for 3 hours at room temperature and then poured into ethyl ether and washed with 1 M NaOH (5×50mL). The ether extracts were dried over $MgSO_4$, filtered and the solvent was removed in vacuo to produce 0.30 g of N,N-dimethyl benzylamine as a yellowish oil (74% yield).

EXAMPLE 11 (PREPARATION OF N-BENZYLPYRROLE)

N-benzylsuccinimide (0.38 g, 2.0 mmol), triethoxysilane (1.85 mL, 10 mmol), and titanium (IV) isopropoxide (0.06 mL, 0.2 mmol) were dissolved in $C_6H_6$ (4.0 mL) and the mixture was heated to 60 ° C. for 16 hours. The solvent was removed in vacuo and the reaction mixture was poured into a mixture of 1 M NaOH (10 mL) and THF (10 mL). This mixture was stirred for 1 hour, poured into ethyl ether (75 mL), and washed with 1 M NaOH (5×50 mL). The ether layer was dried over $MgSO_4$, filtered, and the solvent was removed in vacuo to produce 0.29 g (91% yield) of N-benzylpyrrole as a yellow oil.

EXAMPLE 12 (PREPARATION OF CHRYSANTHEMUMYL ALCOHOL)

A dry Schlenk tube under argon was charged with trichlorotitanium (IV) isopropoxide (35 mg, 0.25 mmol) and triethoxysilane (1.38 mL, 7.5 mmol) and heated to 40° C. Ethyl chrysanthemumate (650 μL, 3 mmol) was then added, and the reaction mixture was stirred at 40° C. After 4 days, the reaction was not yet complete. An additional 300 μL of triethoxysilane was added. After an additional 24 hours, standard work-up afforded 429 mg (93% yield) of a yellow oil, a mixture of cis and trans isomers of chrysanthemumyl alcohol, which was >90% pure by NMR analysis.

EXAMPLE 13 (PREPARATION OF DECANOL)

A dry Schlenk tube under argon was charged with 48 mg (0.15 mmol) of niobium (V) ethoxide. Triethoxysilane (1.4 mL, 7.5 mmol) and ethyl decanoate (696 μL, 3 mmol) were added and the reaction mixture was heated to 50° C. After 3 hours, the reaction was complete, as determined by GLC analysis of an aliquot taken from the reaction mixture. THF (8 mL) and aqueous NaOH (1 N, 15mL) were then added, and the mixture was stirred vigorously for 3.5 hours. The reaction was worked up as follows: The reaction mixture was added to a water/ether mixture (50 mL each) and shaken vigorously. The two layers were separated, and the aqueous layer was extracted with an additional 50 mL of ether. The combined organic layers were then dried over $MgSO_4$, filtered, and concentrated. Purification by flash chromatography (ether:hexane=1:1) afforded 370 mg of a clear oil with a flaky precipitate suspension. Filtering the oil through a small plug of celite afforded 343 mg (72% yield) of pure decanol product (>95% pure by $^1H$-NMR analysis).

EXAMPLE 14 (PREPARATION OF CHRYSANTHEMUMYL ALCOHOL)

A dry Schlenk tube under argon was charged with 48 mg (0.15 mmol) of niobium (V) ethoxide. Triethoxysilane (1.4 mL, 7.5 mmol) and ethyl chrysanthemumate (650 μL, 3 mmol) were added and the reaction mixture was heated to 50° C. After 5 days, the reaction was complete, as determined by GLC analysis of an aliquot taken from the reaction mixture. THF (8 mL) and aqueous NaOH (1 N, 15 mL) were then added, and the mixture was stirred vigorously for 4 hours. The reaction was worked up as in Example 13. Purification by flash chromatography (ether:hexane=1:1) afforded 320 mg (69% yield) of a yellow oil, a mixture of cis and trans isomers of chrysanthemumyl alcohol (>95% pure by $^1H$-NMR analysis).

EXAMPLE 15 (PREPARATION OF DECANOL)

A dry Schlenk tube under argon was charged with 48 mg (0.15 mmol) of neodymium (III) isopropoxide. Triethoxysilane (1.4 mL, 7.5 mmol) and ethyl decanoate (696 μL, 3 mmol) were added and the reaction mixture was heated to 60° C. After 7 hours exposure of the reaction mixture to air caused a flame, presumably due to SiH₄ gas evolution. After 29 hours, THF (8 mL) and aqueous NaOH (1 N, 15 mL) were added, and the mixture was stirred vigorously for 2.5 hours. The reaction was worked up as in Example 13. Purification by flash chromatography (ether:hexane=3:7) afforded 114 mg (24% yield) of pure decanol and 263 mg (44% yield) of recovered starting material (both >95% pure by ¹H-NMR analysis).

EXAMPLE 16 (PREPARATION OF DECANOL)

A dry Schlenk tube under argon was charged with 51 mg (0.15 mmol) of dysprosium (III) isopropoxide. Triethoxysilane (1.4 mL, 7.5 mmol) and ethyl decanoate (696 µL, 3 mmol) were added and the reaction mixture was heated to 60° C. After 29 hours, GLC analysis of an aliquot taken from the reaction mixture showed 23% conversion. The reaction mixture was then heated to 70° C. After an additional 3 days, THF (8 mL) and aqueous NaOH (1 N, 15 mL) were added, and the mixture was stirred vigorously for 3 hours. The reaction was worked up as in Example 13. Purification by flash chromatography (ether:hexane=3:7) afforded 224 mg (47% yield) of decanol (>95% pure by ¹H-NMR analysis) and 40 mg of recovered starting material (84% pure, 5.5% yield).

EXAMPLE 17 (PREPARATION OF 4-PHENYL-2-BUTANOL)

A dry Schlenk tube under argon was charged with 48 mg (0.15 mmol) of neodymium (III) isopropoxide. Triethoxysilane (1.4 mL, 7.5 mmol) was added, and the reaction mixture was heated to 60° C. After 0.5 hours, 4-phenyl-2-butanone (450 µL, 3 mmol) was added. After 24 hours, the reaction was complete, as determined by GLC analysis of an aliquot taken from the reaction mixture. THF (8 mL) and aqueous NaOH (1 N, 15 mL) were added, and the mixture was stirred vigorously for 12 hours. The mixture was added to water and ether (50 mL of each), shaken vigorously, and separated. The aqueous layer was then extracted with an additional 50 mL of ether, and the combined organic layers were dried over MgSO₄. After removal of the drying agent by filtration and concentration of the solution by rotary evaporation, the crude material was purified by flash chromatography (ether:hexane=3:7) to afford 245 mg (54% yield) of 4-phenyl-2-butanol (>95% pure by ¹H-NMR analysis).

EXAMPLE 18 (PREPARATION OF 4-PHENYL-2-BUTANOL)

A dry Schlenk tube under argon was charged with 51 mg (0.15 mmol) of dysprosium (III) isopropoxide. Triethoxysilane (1.4 mL, 7.5 mmol) was added, and the reaction mixture was heated to 60° C. After 0.5 hours, 4-phenyl-2-butanone (450 µL, 3 mmol) was added. After 24 hours, the reaction was complete, as determined by GLC analysis of an aliquot taken from the reaction mixture. THF (8 mL) and aqueous NaOH (1 N, 15 mL) were added, and the mixture was stirred vigorously for 12 hours. After work-up as in Example 13, the crude material was purified by flash chromatography (ether:hexane=3:7) to afford 234 mg (52% yield) of 4-phenyl-2-butanol (>95% pure by ¹H-NMR analysis).

EXAMPLE 19 (PREPARATION OF 4-PHENYL-2-BUTANOL)

A dry Schlenk tube under argon was charged with 37 mg (0.15 mmol) of yttrium (III) isopropoxide ($Y_5O(i-PrO)_{13}$). Triethoxysilane (1.4 mL, 7.5 mmol) was added, and the reaction mixture was heated to 60° C. After 0.5 hours, 4-phenyl-2-butanone (450 µL, 3 mmol) was added. After 24 hours, the reaction was complete, as determined by GLC analysis of a aliquot taken from the reaction mixture. THF (8 mL) and aqueous NaOH (1 N, 15 mL) were added, and the mixture was stirred vigorously for 12 hours. After work-up as in Example 13, the crude material was purified by flash chromatography (ether:hexane=3:7) to afford 235 mg (of 4-phenyl-2-butanol (>93% pure by ¹H-NMR analysis, 48% adjusted yield).

With respect to the above examples, it is noted that the hexane used was deolefinated by stirring over $H_2SO_4$ and stored over $CaH_2$ before distillation from sodium/benzophenone ketyl under argon. Also, benzene solvent was distilled from sodium/benzophenone under argon.

Moreover, it is understood that the above examples are intended to be illustrative of the invention and should not be read to limit the invention to the specific reduction reactions provided in the examples. One skilled in the art will readily appreciate that the invention is applicable to a variety of reduction reactions in which the substrate is an ester, a lactone, a ketone, an amide, or an imide, and that a variety of catalysts may be used in these reduction reactions.

While many of the examples demonstrating the reduction of esters to alcohols were conducted in air, it is understood that such reactions may be conducted in an inert atmosphere, such as argon or nitrogen, as well.

What is claimed is:

1. A process for catalytically reducing organic carbonyl compounds, comprising the steps of:
   providing a stoichiometric quantity of a silane reducing agent able to contribute a hydride ion during the reduction reaction, a catalytic amount of a catalyst selected from the group consisting of M(L) (L') (L''), M(L) (L') (L'') (L'''), M(L) (L') (L'') (L''') (L$^{iv}$), and M(L) (L') (L'') (L''') (L$^{iv}$) (L$^v$), where M is a group 3, 4, 5 or 6 metal, a lanthanide or an actinide and L, L', L'', L''', L$^{iv}$, L$^v$, independently, are some combination of H, an alkyl, an aryl, a silyl, a halogen, —OR, —SR, or —NR(R'), where R and R' are H, an alkyl or aryl and are different or the same, and a stoichiometric quantity of an organic carbonyl substrate selected from the group consisting of esters, lactones, amides and imides;
   reacting the organic carbonyl substrate in the presence of the catalyst and the silane compound at a temperature between 25° and 80° C.; and
   recovering and purifying the reaction product.

2. The process of claim 1 wherein the catalyst is a metal alkoxide or a metal aryloxide complex.

3. The process of claim 2 wherein said catalyst is selected from the group consisting of titanium (IV) isopropoxide, titanium (IV) ethoxide, and trichlorotitanium (IV) isopropoxide.

4. The process of claim 1 wherein the silane reducing agent is selected from the group consisting of diphenylsilane, phenylsilane, diethylsilane, dimethylsilane, triethoxysilane, trimethoxysilane, and poly(methylhydroxysiloxane).

5. The process of claim 4 wherein the silane reducing agent is present in an amount ranging from about 100 to 300 percent by mole, relative to the substrate.

6. The process of claim 5 wherein the catalyst is present in an amount ranging between about 3 and 10 percent by mole, relative to the substrate.

7. The process of claim 1 wherein an ester substrate is reduced to an alcohol.

8. The process of claim 7 wherein following the step of reacting the substrate with the silane compound in the presence of the catalyst, the process further comprises the step of cleaving silicon from the resulting reaction product.

9. The process of claim 1 wherein a lactone substrate is reduced to a diol.

10. The process of claim 9, wherein following the step of reacting the substrate in the presence of the catalyst and the silane compound, the process further comprises the step of cleaving silicon from the resulting reaction product.

11. The process of claim 1 wherein following the step of reacting the substrate in the presence of the catalyst and the silane compound, the process further comprises the step of cleaving silicon from the resulting reaction product.

12. The process of claim 1 wherein an amide substrate, having an alpha hydrogen, is reduced to an enamine.

13. The process of claim 1 wherein an amide substrate is reduced to an amine.

14. The process of claim 1 wherein an imide substrate is reduced to a dienamine.

15. The process of claim 2 wherein the catalyst is selected from the group consisting of niobium (V) ethoxide, neodymium (III) isopropoxide, dysprosium (III) isopropoxide, and yttrium (III) isopropoxide.

16. A process for catalytically reducing organic carbonyl compounds, comprising the steps of:

providing a stoichiometric quantity of a silane reducing agent able to contribute a hydride ion during the reduction reaction, a catalytic amount of an air stable catalyst selected from the group consisting of M(L) (L') (L''), M(L) (L') (L'') (L'''), M(L) (L') (L'') (L''') (L$^{iv}$), and M(L) (L') (L'') (L''') (L$^{iv}$) (L$^v$), where M is a group 3, 4, 5 or 6 metal, a lanthanide or an actinide and L, L', L'', L''', L$^{iv}$, L$^v$, independently, are some combination of H, an alkyl, an aryl, a silyl, a halogen, —OR, —SR, or —NR(R'), where R and R' are H, an alkyl or aryl and are different or the same, and a stoichiometric quantity of an organic carbonyl substrate selected from the group consisting of esters, lactones, amides and imides;

reacting the organic carbonyl substrate in the presence of the catalyst and the silane compound at a temperature between 25° and 80° C.; and recovering and purifying the reaction product.

* * * * *